United States Patent [19]
Green, II

[11] Patent Number: 5,145,521
[45] Date of Patent: Sep. 8, 1992

[54] SULFURIC ACID/POLYAMIDE COMPOSITIONS

[75] Inventor: James A. Green, II, Chino, Calif.

[73] Assignee: Union Oil Company of California, Los Angeles, Calif.

[21] Appl. No.: 712,913

[22] Filed: Jun. 7, 1991

[51] Int. Cl.$^5$ .................. C08K 3/24; C08L 89/00; C09D 189/00

[52] U.S. Cl. ..................... 106/161; 106/135; 423/523; 423/527

[58] Field of Search ............... 106/135, 161; 524/422; 423/523, 527

[56] References Cited

U.S. PATENT DOCUMENTS

| | | | |
|---|---|---|---|
| 2,423,773 | 7/1947 | Hart et al. | 106/135 |
| 3,206,439 | 9/1965 | Detoro et al. | 524/422 |
| 3,269,970 | 8/1966 | Epstein et al. | 524/422 |
| 3,804,791 | 4/1974 | Morgan | 524/422 |
| 3,836,498 | 9/1974 | Gulrich et al. | 524/422 |
| 3,869,419 | 3/1975 | Morgan et al. | 524/422 |
| 4,320,081 | 3/1982 | Lammers | 524/422 |
| 4,397,675 | 8/1983 | Young . | |
| 4,402,852 | 9/1983 | Young . | |
| 4,404,116 | 9/1983 | Young . | |
| 4,445,925 | 5/1984 | Young . | |
| 4,447,253 | 5/1984 | Young . | |
| 4,664,717 | 5/1987 | Young . | |
| 4,673,522 | 6/1987 | Young . | |
| 4,722,986 | 2/1988 | Young . | |

OTHER PUBLICATIONS

*The Condensed Chemical Dictionary*, 7th Ed., (New York: Reinhold, pp. 443-444, '73.

*Primary Examiner*—Theodore Morris
*Assistant Examiner*—David M. Brunsman
*Attorney, Agent, or Firm*—Gregory F. Wirzbicki; William M. Dooley

[57] ABSTRACT

Solutions of sulfuric acid having a polyamide, such as gelatin, dissolved therein are less corrosive than polyamide-free solutions of sulfuric acid of equal sulfuric acid concentration, while retaining essentially all of the acidity. The polyamide-safened sulfuric acid solutions of the invention are useful in place of sulfuric acid solutions for many purposes, e.g., as cleaners and herbicides, and for the treatment of cellulosic materials.

31 Claims, No Drawings

SULFURIC ACID/POLYAMIDE COMPOSITIONS

FIELD OF THE INVENTION

This invention relates to safened compositions comprising concentrated sulfuric acid and a polyamide, preferably a polyamide of alpha-amino acid, such as gelatin, and to methods of use thereof. The compositions can be used in place of untreated sulfuric acid, for example, as herbicides and cleaners.

INTRODUCTION

Sulfuric acid is used for many purposes in industry and agriculture. For example, it is used as a herbicide, a drain cleaner, a pickling acid, and a catalyst for many organic reactions. Concentrated sulfuric acid is very hazardous to workers, producing rapid skin burns. It also chars hydroxyl-rich compounds such as cellulose and carbohydrates on contact by abstracting water from the molecules of the compounds.

Adducts of sulfuric acid with urea, biuret, and triuret, and method of using such adducts, have been disclosed. See U.S. Pat. Nos. 4,722,986, 4,673,522, 4,664,717, 4,402,852, 4,404,116, 4,445,925, 4,447,253, and 4,397,675, the disclosures of which are incorporated by reference herein in their entirety. Such adducts are much less corrosive and hazardous than sulfuric acid of equivalent acid concentration, yet they retain essentially all the acidity of the sulfuric acid. In effect, the activity of the sulfuric acid is moderated or safened without neutralization of the acid.

SUMMARY OF THE INVENTION

It has now been found that safened compositions in which the activity of concentrated solutions of sulfuric acid is moderated can be prepared by dissolving therein therein a polyamide or mixtures thereof, preferably a polyamide of an alpha-amino acid or mixtures thereof, most preferably gelatin.

The compositions are useful as broad spectrum herbicides and as cleaners in applications where sulfuric acid can be used. They are also capable of dissolving cellulosic materials without charring, and are thus useful for treating agricultural products, e.g., for scarifying seeds, delinting cotton seeds, softening wood pulp, and converting or softening cellulosic materials to a form suitable for incorporation into animal feeds. The polyamide itself provides a beneficial source of nitrogen for animal feeds and for soil treated with herbicides of the invention.

DETAILED DESCRIPTION OF THE INVENTION

Compositions of this invention are made by simply dissolving a polyamide in sulfuric acid. Usually, and most preferably, standard commercial concentrated sulfuric acid, i.e., about 98 weight percent, is used. Throughout the specification and the claims, the term "concentrated sulfuric acid" shall mean such standard commercial concentrated sulfuric acid of about 98 weight percent concentration. More concentrated sulfuric acid, such as anhydrous sulfuric acid, and even oleum, a solution of sulfur trioxide in sulfuric acid, can be used. Surprisingly, the polyamide, e.g., gelatin, dissolves in concentrated sulfuric acid smoothly, without charring, to produce a colored, viscous, but clear solution.

An polyamide that is soluble in concentrated sulfuric acid, preferably at ambient temperature, can be used with benefit in the practice of this invention. The polyamide can be substituted with groups stable in sulfuric acid, such as alkoxy, hydroxy, and halogen. The nature of any substituents present is unimportant for the purpose of this invention so long as the substituents do not react so adversely with sulfuric acid as to render the composition useless for its intended purpose. For example, some degradation of the polyamide may be acceptable in a drain cleaner, but when the compositions are to be used as herbicides, the polyamides preferably have only substituents which do not react with concentrated sulfuric acid or, more preferably, are unsubstituted.

Suitable polyamides can be prepared from polyfunctional compounds or mixtures thereof comprising amino groups and carboxylic acid groups, such as polyamines, polycarboxylic acids, and amino acids, and by polymerization of lactams such as caprolactam and 2-pyrrolidone. Difunctional compounds, e.g., diamines, dicarboxylic acids, and amino acids having one amino group and one carboxylic acid group per molecule, are preferred because they form linear polyamides, i.e., polyamides having little or no crosslinking. Linear polyamides are preferred, since crosslinking can diminish the solubility of the polyamide. Suitable polyamides and methods of making suitable polyamides are well known. See, for example, *Kirk-Othmer Encyclopedia of Chemical Technology*, 3d Ed. (New York: John Wiley & Sons), Vol. 18, pp. 328–371, the disclosure of which is incorporated herein by reference in its entirety. Many suitable polyamides are commercially available, such as the large family of polyamides known as nylons, which are reaction products of diamines and dicarboxylic acids.

Aside from solubility in sulfuric acid, the most important property of the polyamide used in the practice of this invention is the weight percentage of amido nitrogen in the polyamide. Preferably, the amido nitrogen constitutes at least about 5 weight percent, more preferably at least about 10 percent, even more preferably at least about 15 percent, and most preferably at least about 20 percent of the total weight of polyamide. About the highest possible percentage of amido nitrogen, 28 percent, would occur in a polyamide made from diaminomethane and oxalic acid. Approaching that level is polyglycine, which has a repeating unit of the formula

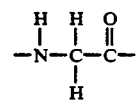

This unit has a total molecular weight of 57. The amido nitrogen content is thus $(14/57) \times 100 = 24.6$ weight percent.

Polyamides of alpha-amino carboxylic acids (sometimes called "amino acids" herein) and mixtures of such acids are preferred. Alpha-amino acids can be represented by the formula

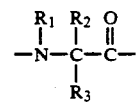

wherein $R_1$, $R_2$, and $R_3$ independently represent substituents which do not react so adversely with concentrated sulfuric acid as to render the composition unfit for its intended use. Preferably, the substituents are substantially inert to concentrated sulfuric acid, at least at ambient temperature, i.e., below about 90° F. (32° C.). The combined weight of the three substituents is typically no more than about 226 (amido N content at least about 5%), preferably no more than about 86 (amido N content at least about 10%), and more preferably no more than about 16 (amido N content at least about 20%). When polyamides of mixtures of amino acids are used, the combined weight of the three substituents refers to the average combined weight thereof in the polyamide.

$R_1$, $R_2$, and $R_3$ independently are preferably hydrogen or alkyl groups having up to about 16 carbon atoms, preferably no more than about 8 carbon atoms, more preferably no more than about 2 carbon atoms. Even more preferably, one of $R_1$, $R_2$, and $R_3$ is a methyl group, usually $R_2$ or $R_3$, and the other two are hydrogen. Most preferably, all three are hydrogen.

Proteins constitute a large class of naturally occurring polyamides of alpha-amino acids, typically comprising mixtures of many different amino acids. Compositions of the invention which need not be especially pure, for example a drain cleaner, may be made by dissolving naturally occurring proteins or protein containing materials, such as soy protein, leather, or animal by-products, in concentrated sulfuric acid.

Any kind or grade of gelatin can be used in preparing compositions of the invention. Gelatin is commercially available in various grades prepared from various starting materials. Properties and preparation of gelatin are described in the technical literature, for example, *Kirk-Othmer Encyclopedia of Chemical Technology*, 3d Ed. (New York: John Wiley & Sons), Vol. 11, pp. 711–719, the disclosure of which is incorporated herein by reference in its entirety. Gelatin contains a substantial proportion of the amino acid glycine, but usually also contains other amino acids as well, the type and distribution thereof being influenced by the source materials from which the gelatin is derived. Commercial gelatin typically contains between about 26.4 and about 30.5 weight percent glycine, between about 14.8 and about 18 percent proline, and between about 13.3 and about 14.5 percent glutamic acid. In general, any form of gelatin is satisfactory for preparing compositions to be used as herbicides and heavy cleaners. More refined grades of gelatin, e.g., food grade gelatin, may be used where a composition of higher purity is desired. There are two principal types of gelatin, both of which are suitable for use in the practice of this invention: Type A, produced by acid hydrolysis of collagen; and Type B, produced by alkaline hydrolysis of collagen. The collagen is obtained from a variety of animal by-products, mainly bones and hides.

Gelatin has the unusual property of undergoing a reversible gel to sol transition in aqueous solution, making it especially useful for preparing sulfuric acid compositions of high viscosity that can adhere to substrates without running or sagging.

Other hydrolysates of collagen include animal glue and liquid protein. These differ from gelatin in that they have lower average molecular weights and do not undergo the gel to sol transformation. They are useful for preparing compositions of the invention which need not have the highest viscosity or gel-forming properties, but which display the desired moderated acid activity.

Compositions of the invention can be made simply by dissolving the polyamide, e.g., gelatin, directly in sulfuric acid. Usually, aqueous sulfuric acid having an initial concentration of at least about 50 weight percent is used. Preferably, the sulfuric acid has an initial concentration of at least about 75 percent, and more preferably at least about 90 percent. Most preferred is concentrated sulfuric acid, i.e., sulfuric acid having an initial concentration of at least about 98 weight percent, such as ordinary commercial concentrated sulfuric acid. Ambient temperatures, e.g., between about 10° and 30° C., are usually satisfactory, although higher temperatures can be used to speed the process. Moderate agitation such as stirring is useful.

Stable surfactants can be included in the compositions. Suitable surfactants are described in U.S. Pat. No. 4,722,986, from column 8, line 66 through column 9, line 68. Briefly, classes of stable surfactants include nonionics such as the alkylphenol polyethylene oxides, anionics such as the long chain alkyl sulfates, and cationics such as 1-hydroxyethyl-2-heptadecenyl gloxalidin. Of these, the polyethylene oxide nonionic surfactants are particularly preferred.

The surfactant concentration is preferably sufficient to increase the ability of the sulfuric acid/polyamide compositions to wet the material to be treated. Even very minor surfactant concentrations increase the wetting ability of the compositions to some extent. Surfactant concentration will usually be at least about 0.05, generally at least about 0.1, and preferably at least about 0.2 weight percent of the solution as it is employed in the methods of this invention. Surfactant concentrations of about 0.2 to about 1 weight percent are adequate in most applications.

The compositions of the invention can be used full strength, or they can be diluted before use, usually with water. Diluted compositions typically comprise from about 5 weight percent to about 95 weight percent added water. The degree of dilution is usually chosen to suit a particular use of the composition.

When the compositions are used as herbicides, they are applied to plants, preferably to the foliage thereof, in a sufficient quantity and concentration to kill the plants, or at least to retard or stop the growth or reproduction thereof. Herbicidal compositions typically have an equivalent sulfuric acid concentration of at least about 10 weight percent, preferably at least about 20 percent, and more preferably at least about 40 percent; and a polyamide concentration of at least about 2 weight percent, preferably at least about 5 percent, and more preferably at least about 10 percent. Such compositions are typically applied at the rate of at least about 5 gallons per acre (47 liters per hectare), preferably at least about 10 gallons per acre (93 liters per hectare), more preferably at least about 20 gallons per acre (187 liters per hectare). Optimum application rates depend upon many factors and must necessarily be worked out on a case by case basis.

Compositions suitable for heavy cleaning operations, e.g., drain cleaning and rust removal, usually have equivalent sulfuric acid concentration of at least about 5 weight percent, preferably at least about 10 percent, and more preferably at least about 20 percent; a polyamide content of at least about 1 weight percent, preferably at least about 2 percent, and more preferably at least about 5 percent; and a water content of at least about 1 weight percent, preferably at least about 10 percent, and more preferably at least about 20 percent. The water content of these compositions assists in the cleaning function.

Compositions suitable for treating cellulosic materials, e.g., for delinting cotton seeds or softening animal fodder, usually have an equivalent sulfuric acid concentration of at least about 5 weight percent sulfuric acid, preferably at least about 10 percent, and more preferably at least about 20 percent; a polyamide content of at least about 1 weight percent polyamide, preferably at least about 2 percent, and more preferably at least about 5 percent; and a water content of at least about 1 weight percent, preferably at least about 5 percent, and more preferably at least about 10 percent.

Surprisingly, as demonstrated in Example 3, compositions of the invention consisting essentially of concentrated sulfuric acid and a polyamide, i.e., gelatin, are capable of dissolving cellulose without charring. The addition of a small proportion of water to the composition further increases the solubility of cellulose therein. Thus for the dissolution of cellulosic materials, suitable compositions comprise between about 50 and 78 weight percent $H_2SO_4$, preferably between about 55 and 65 percent; between about 5 and about 30 weight percent gelatin, preferably between about 10 and about 25 percent gelatin; and between about 0.5 and about 20 weight percent water, preferably between about 5 and about 15 percent water. In these compositions, the solubility of cellulose therein increases with increasing water content within the preferred proportions. However, excessive dilution of the compositions would diminish the solubility of cellulose therein.

The following examples are intended to illustrate particular embodiments of the invention. The examples are not intended in any way to limit the invention, the scope of which is defined in the appended claims.

EXAMPLE 1

Sufficient gelatin was dissolved in 98 percent sulfuric acid to produce a deep red to brown, viscous solution containing 20 weight percent gelatin. The gelatin dissolved smoothly, without charring.

An 80 weight percent aqueous solution of sulfuric acid causes a burning sensation almost immediately when spread on the tender skin of the forearm. However, when the 80:20 sulfuric acid:gelatin solution is applied to the inner forearm, it produces a burning sensation only after about 1 minute of contact. Thus, the moderated activity and improved safety of the compositions of this invention is evident.

EXAMPLE 2

A solution of gelatin in sulfuric acid was prepared containing 39 weight percent sulfuric acid, 36 percent equivalent glycine (the gelatin regarded as 100% glycine, molecular weight 89), and 25 percent water based on the final formulation.

EXAMPLE 3

About 3.8 grams of cotton dissolved without charring in about 36 grams of a 20 weight percent solution of gelatin in concentrated (98 weight percent) sulfuric acid. About 10 grams of water was added to the resulting solution, enabling an additional 3.4 grams of cotton to be dissolved therein. This demonstrates the utility of these compositions for the delinting of cotton seeds.

While particular embodiments of the invention have been described and illustrated herein, it will be understood that the invention is not limited thereto, since many obvious modifications can be made. This invention is intended to include any such modifications as will fall within the scope and equivalency of the appended claims.

What is claimed is:

1. A composition comprising a protein dissolved in at least about 50 weight percent concentration sulfuric acid.

2. The composition of claim 1 wherein at least about 1 weight percent of said protein, by weight of composition, is dissolved in said sulfuric acid.

3. The composition of claim 1 wherein at least about 5 weight percent of said protein, by weight of composition, is dissolved in said sulfuric acid.

4. The composition of claim 3 wherein at least about 5 weight percent gelatin is dissolved in concentrated sulfuric acid.

5. The composition of claim 1 wherein at least about 10 weight percent of said protein, by weight of composition, is dissolved in said sulfuric acid.

6. The composition of claim 5 wherein at least about 10 weight percent gelatin is dissolved in concentrated sulfuric acid.

7. The composition of claim 1 wherein at least about 20 weight percent of said protein, by weight of composition, is dissolved in said sulfuric acid.

8. The composition of claim 7 wherein at least about 20 weight percent gelatin is dissolved in concentrated sulfuric acid.

9. The composition of claim 1 which comprises a saturated solution of said protein in said sulfuric acid.

10. The composition of claim 9 which comprises a saturated solution of gelatin in concentrated sulfuric acid.

11. The composition of claim 1 wherein said sulfuric acid has an concentration of at least about 75 weight percent.

12. The composition of claim 1 wherein said sulfuric acid has an concentration of at least about 90 weight percent.

13. The composition of claim 1 wherein said sulfuric acid has an concentration of at least about 98 weight percent.

14. A composition comprising an aqueous solution comprising at least about 5 weight percent sulfuric acid and at least about 1 weight percent of said protein prepared by dilution of a composition of claim 9.

15. The composition of claim 14 comprising at least about 10 weight percent sulfuric acid and at least about 2 weight percent of said protein.

16. The composition of claim 15 wherein the protein comprises gelatin.

17. The composition of claim 14 comprising at least about 40 weight percent sulfuric acid and at least about 5 weight percent of said protein.

18. The composition of claim 17 wherein the protein comprises gelatin.

19. The composition of claim 14 wherein the protein comprises gelatin.

20. The composition of claim 13 wherein the protein comprises gelatin.

21. A composition comprising an aqueous solution comprising at least about 5 percent sulfuric acid and at least about 1 weight percent of said protein prepared by dilution of a composition of claim 1.

22. The composition of claim 21 comprising at least about 10 weight percent sulfuric acid and at least about 2 weight percent of said protein.

23. The composition of claim 22 wherein the protein comprises gelatin.

24. The composition of claim 21 comprising at least about 40 weight percent sulfuric acid and at least about 5 weight percent of said protein.

25. The composition of claim 24 wherein the protein comprises gelatin.

26. The composition of claim 21 wherein the protein comprises gelatin.

27. The composition of claim 1 wherein the protein comprises gelatin.

28. A composition comprising the reaction product of a protein and sulfuric acid having an concentration of at least about 50 weight percent.

29. The composition of claim 28 wherein said protein comprises gelatin and said sulfuric acid has an concentration of at least about 98 percent.

30. A composition comprising a mixture of a protein and sulfuric acid having an concentration of at least about 50 percent.

31. The composition of claim 30 wherein said protein comprises gelatin and said sulfuric acid has an concentration of at least about 98 percent.

* * * * *